(12) United States Patent
Jau et al.

(10) Patent No.: US 8,094,924 B2
(45) Date of Patent: Jan. 10, 2012

(54) E-BEAM DEFECT REVIEW SYSTEM

(75) Inventors: Jack Jau, Los Altos Hills, CA (US);
Zhongwei Chen, San Jose, CA (US); Yi Xiang Wang, Fremont, CA (US);
Chung-Shih Pan, Palo Alto, CA (US);
Joe Wang, Campbell, CA (US);
Xuedong Liu, Cupertino, CA (US);
Weiming Ren, San Jose, CA (US); Wei Fang, Milpitas, CA (US)

(73) Assignee: Hermes-Microvision, Inc., Hsinchu (TW)

( * ) Notice: Subject to any disclaimer, the term of this patent is extended or adjusted under 35 U.S.C. 154(b) by 505 days.

(21) Appl. No.: 12/335,458

(22) Filed: Dec. 15, 2008

(65) Prior Publication Data
US 2010/0150429 A1     Jun. 17, 2010

(51) Int. Cl.
G06K 9/00 (2006.01)
(52) U.S. Cl. ........................................ 382/149
(58) Field of Classification Search .................. None
See application file for complete search history.

(56) References Cited

U.S. PATENT DOCUMENTS

| | | | |
|---|---|---|---|
| 4,068,123 A | 1/1978 | Kokubo | |
| 4,675,524 A | 6/1987 | Frosien et al. | |
| 4,700,075 A | 10/1987 | Kurz et al. | |
| 4,713,543 A | 12/1987 | Feuerbaum et al. | |
| 4,728,790 A | 3/1988 | Plies | |
| 4,808,821 A | 2/1989 | Feuerbaum et al. | |
| 4,818,874 A | 4/1989 | Ishikawa | |
| 4,831,266 A | 5/1989 | Frosien et al. | |
| 4,926,054 A | 5/1990 | Frosien | |
| 5,004,918 A | 4/1991 | Tsuno | |
| 5,198,675 A | 3/1993 | Hikita et al. | |
| 5,498,874 A | 3/1996 | Miyoshi et al. | |
| 5,665,968 A | 9/1997 | Meisburger et al. | |
| 5,717,204 A | 2/1998 | Meisburger et al. | |
| 5,872,358 A | 2/1999 | Todokoro et al. | |

(Continued)

FOREIGN PATENT DOCUMENTS

DE    3925949 A1    2/1991

OTHER PUBLICATIONS

Ludwig Reimer, "Image Formation in Low-Voltage Scanning Electron Microscopy", SPIE Optical Engineering Press, Tutorial Texts vol. TT12, 1993, 16 total pages (pp. 12, 13, 28-41, 88-101).

(Continued)

*Primary Examiner* — Tu Nguyen
(74) *Attorney, Agent, or Firm* — Sawyer Law Group, P.C.

(57) ABSTRACT

An apparatus comprises an imaging unit to image a wafer to be reviewed, wherein imaging unit is the modified SORIL column. The modified SORIL column includes a focusing sub-system to do micro-focusing due to a wafer surface topology, wherein the focusing sub-system verifies the position of a grating image reflecting from the wafer surface to adjust the focus; and a surface charge control to regulate the charge accumulation due to electron irradiation during the review process, wherein the gaseous molecules are injected under a flood gun beam rather than under a primary beam. The modified SORIL column further includes a storage unit for storing wafer design database; and a host computer to manage defect locating, defect sampling, and defect classifying, wherein the host computer and storage unit are linked by high speed network.

5 Claims, 8 Drawing Sheets

U.S. PATENT DOCUMENTS

| | | |
|---|---|---|
| 6,194,729 B1 | 2/2001 | Weimer |
| 6,365,896 B1 | 4/2002 | van der Mast |
| 6,380,546 B1 | 4/2002 | Petrov et al. |
| 6,392,231 B1 | 5/2002 | Chen |
| 6,407,387 B1 | 6/2002 | Frosien et al. |
| 6,426,501 B1 | 7/2002 | Nakagawa |
| 6,462,467 B1 | 10/2002 | Russ |
| 6,463,124 B1 | 10/2002 | Weisman et al. |
| 6,545,277 B1 | 4/2003 | Kella et al. |
| 6,605,805 B2 | 8/2003 | Chen |
| 6,617,579 B2 | 9/2003 | Yonezawa |
| 6,642,520 B2 | 11/2003 | Kimura et al. |
| 6,768,324 B1 | 7/2004 | Yamada et al. |
| 6,775,452 B2 | 8/2004 | Howells |
| 6,853,143 B2 | 2/2005 | Nakasuji et al. |
| 6,855,938 B2 | 2/2005 | Preikszas et al. |
| 6,960,766 B2 | 11/2005 | Chen |
| 6,972,412 B2 | 12/2005 | Scholtz et al. |
| 6,975,125 B2 | 12/2005 | Yamada et al. |
| 7,067,807 B2 | 6/2006 | Petrov et al. |
| 7,098,468 B2 | 8/2006 | Aloni et al. |
| 7,161,667 B2 | 1/2007 | Meeks et al. |
| 7,180,317 B2 | 2/2007 | Hollman |
| 7,312,449 B2 | 12/2007 | Nakasuji et al. |
| 7,385,195 B2 | 6/2008 | Yamada et al. |
| 7,521,700 B2 | 4/2009 | Aloni et al. |
| 7,544,937 B2 | 6/2009 | Frosien |
| 7,598,499 B2 | 10/2009 | Platzgummer |
| 7,612,337 B2 | 11/2009 | Suzuki et al. |
| 7,645,989 B2 | 1/2010 | Bihr et al. |
| 7,652,263 B2 | 1/2010 | Feuerbaum |
| 7,705,298 B2 | 4/2010 | Liu et al. |
| 7,705,301 B2 | 4/2010 | Tseng et al. |
| 7,745,784 B2 * | 6/2010 | Nakasuji et al. .............. 250/310 |
| 7,759,653 B2 | 7/2010 | Chen et al. |
| 7,880,143 B2 * | 2/2011 | Tanimoto et al. ............. 250/310 |
| 2003/0155509 A1 | 8/2003 | Nakasuji et al. |
| 2004/0239347 A1 | 12/2004 | Yamada et al. |
| 2005/0023491 A1 | 2/2005 | Young et al. |
| 2005/0133733 A1 | 6/2005 | Nakasuji et al. |
| 2006/0202119 A1 | 9/2006 | Yamada et al. |
| 2006/0243918 A1 | 11/2006 | Aloni et al. |
| 2008/0067380 A1 | 3/2008 | Ozawa et al. |
| 2008/0099693 A1 | 5/2008 | Platzgummer |
| 2008/0217529 A1 | 9/2008 | Sukegawa et al. |
| 2008/0315094 A1 | 12/2008 | Wang et al. |
| 2009/0090866 A1 | 4/2009 | Zhang et al. |
| 2009/0242792 A1 | 10/2009 | Hosoya et al. |
| 2009/0294664 A1 | 12/2009 | Chen et al. |
| 2010/0028235 A1 | 2/2010 | Qin et al. |
| 2010/0102227 A1 | 4/2010 | Chen et al. |
| 2010/0118310 A1 | 5/2010 | Matsui |
| 2010/0150429 A1 | 6/2010 | Jau et al. |

OTHER PUBLICATIONS

K. Tsuno, "Aberration Analysis of a Wien Filter for Electrons", Wissenschaftliche Verlagsgesellschaft mbH Stuugart, vol. 89—No. 1, 1991, pp. 31-40.

Ronnie Porat, et al., "SEM-based methodology for root cause analysis of wafer edge and bevel defects", IEEE/SEMI Advanced Semiconductor Manufacturing Conference, pp. 11-12, 2008.

Jaime D. Morillo, et al., "Edge and Bevel Automated Defect Inspection for 300mm Production Wafers in Manufacturing", IEEE/SEMI Advanced Semiconductor Manufacturing Conference, pp. 1-4, 2005.

* cited by examiner

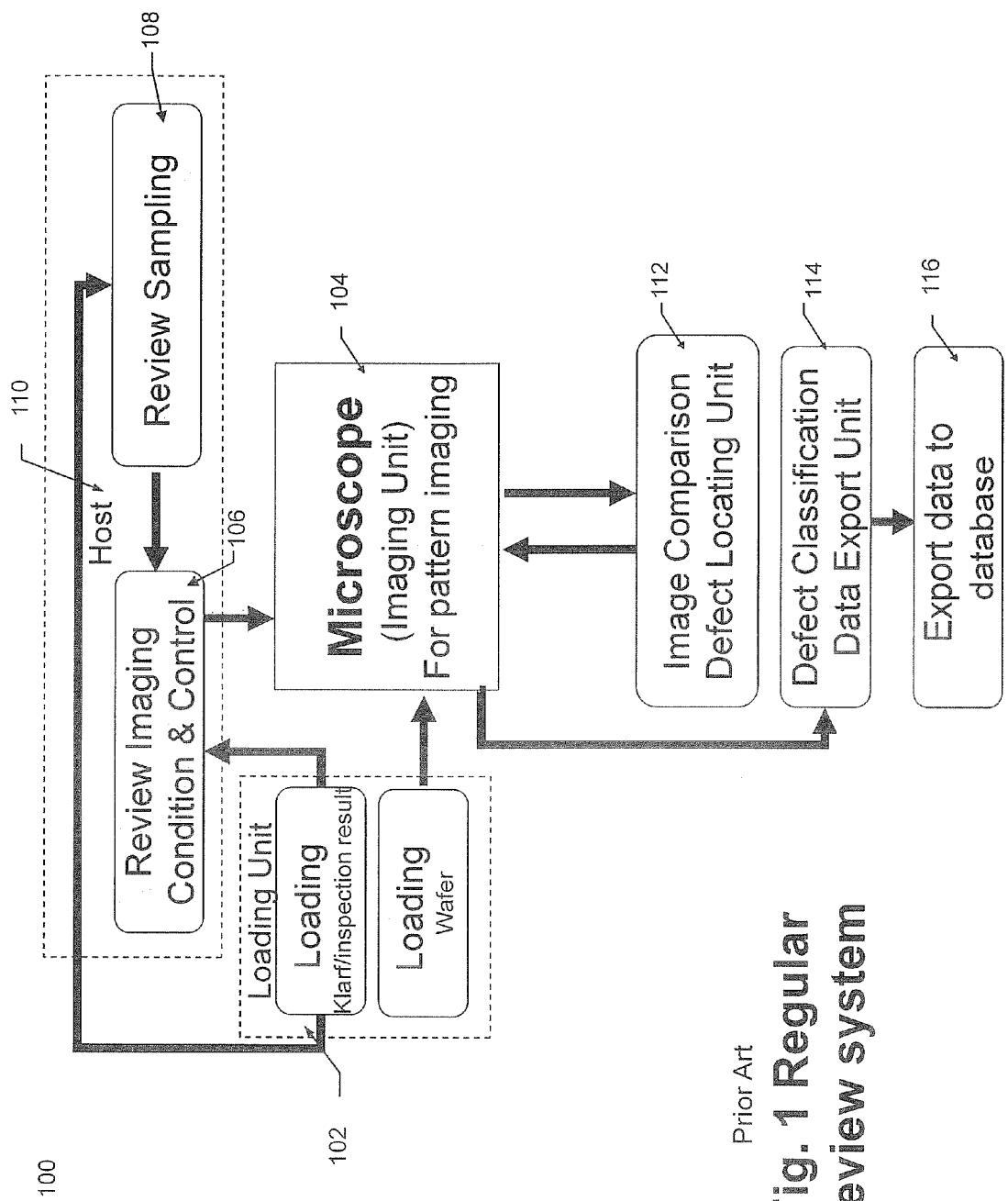
Prior Art
Fig. 1 Regular review system

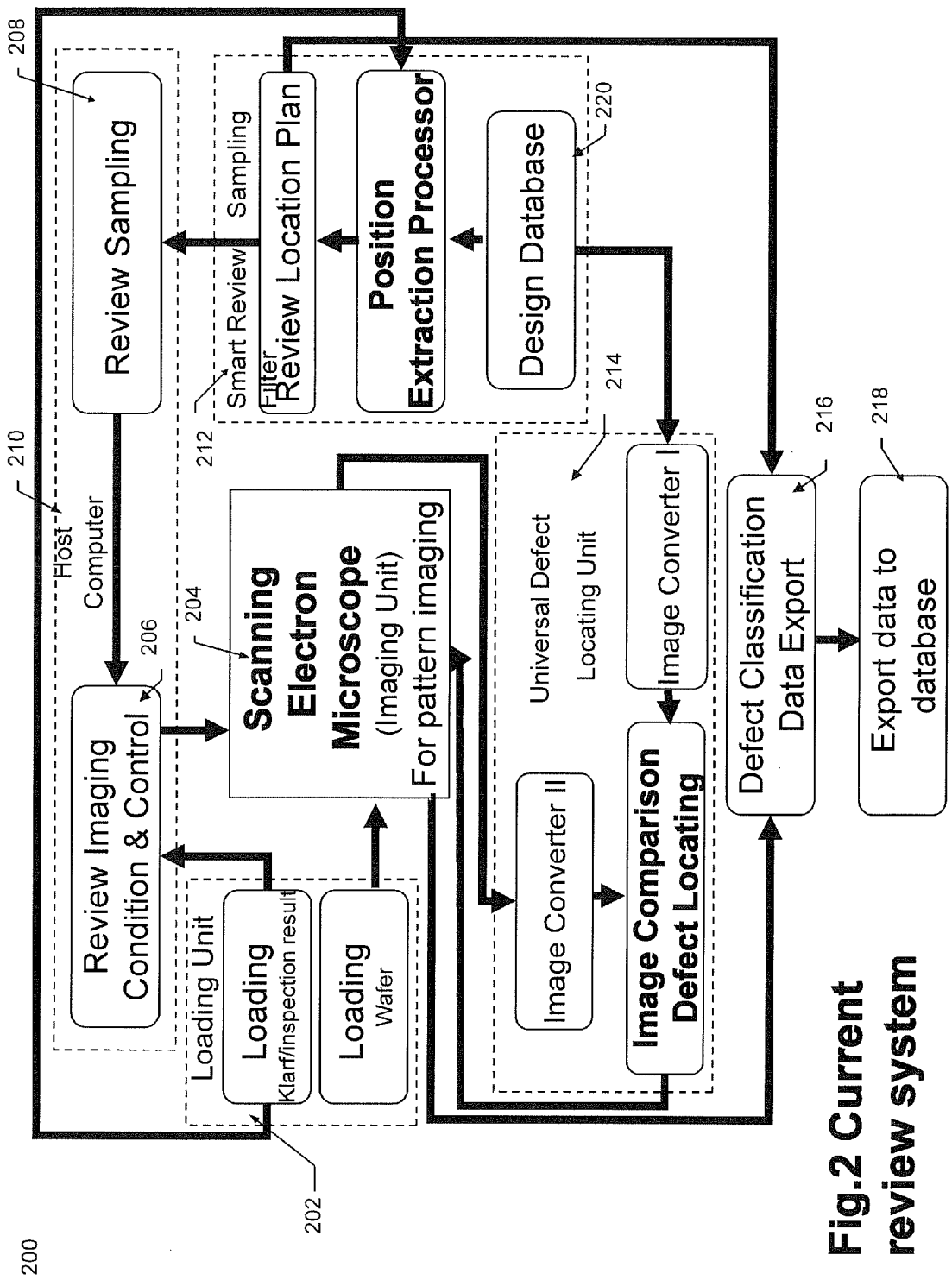
Fig.2 Current review system

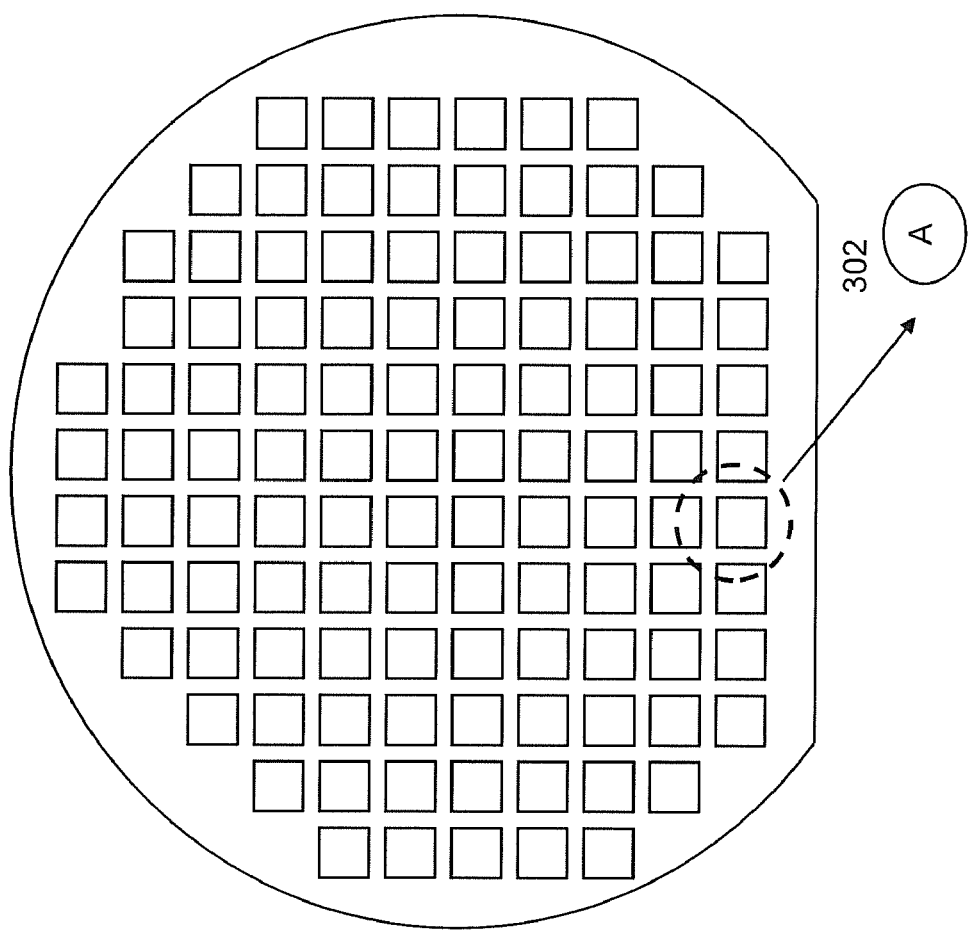
Figure 3: A typical patterned wafer

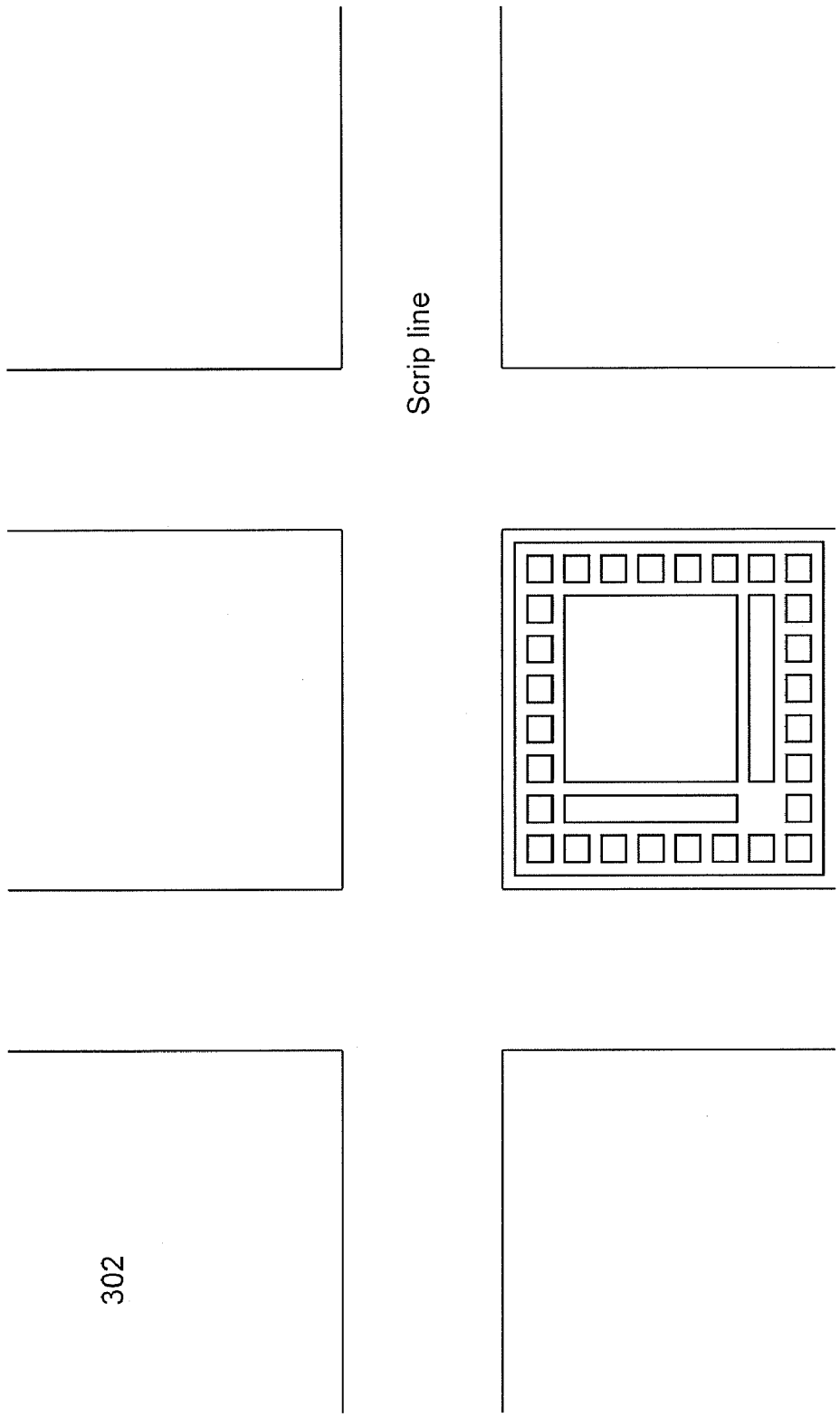
Figure 3a: the enlarge area A

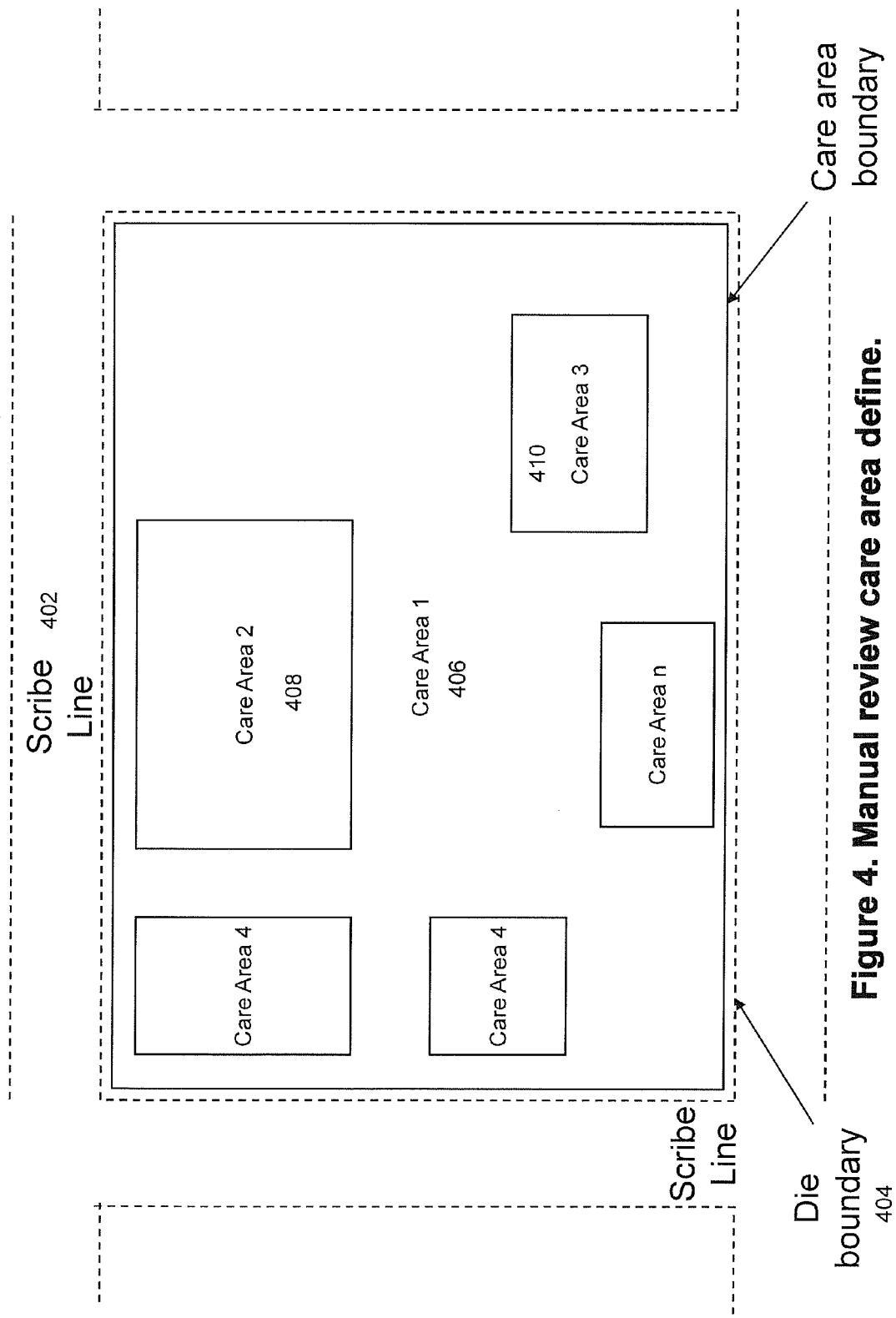
Figure 4. Manual review care area define.

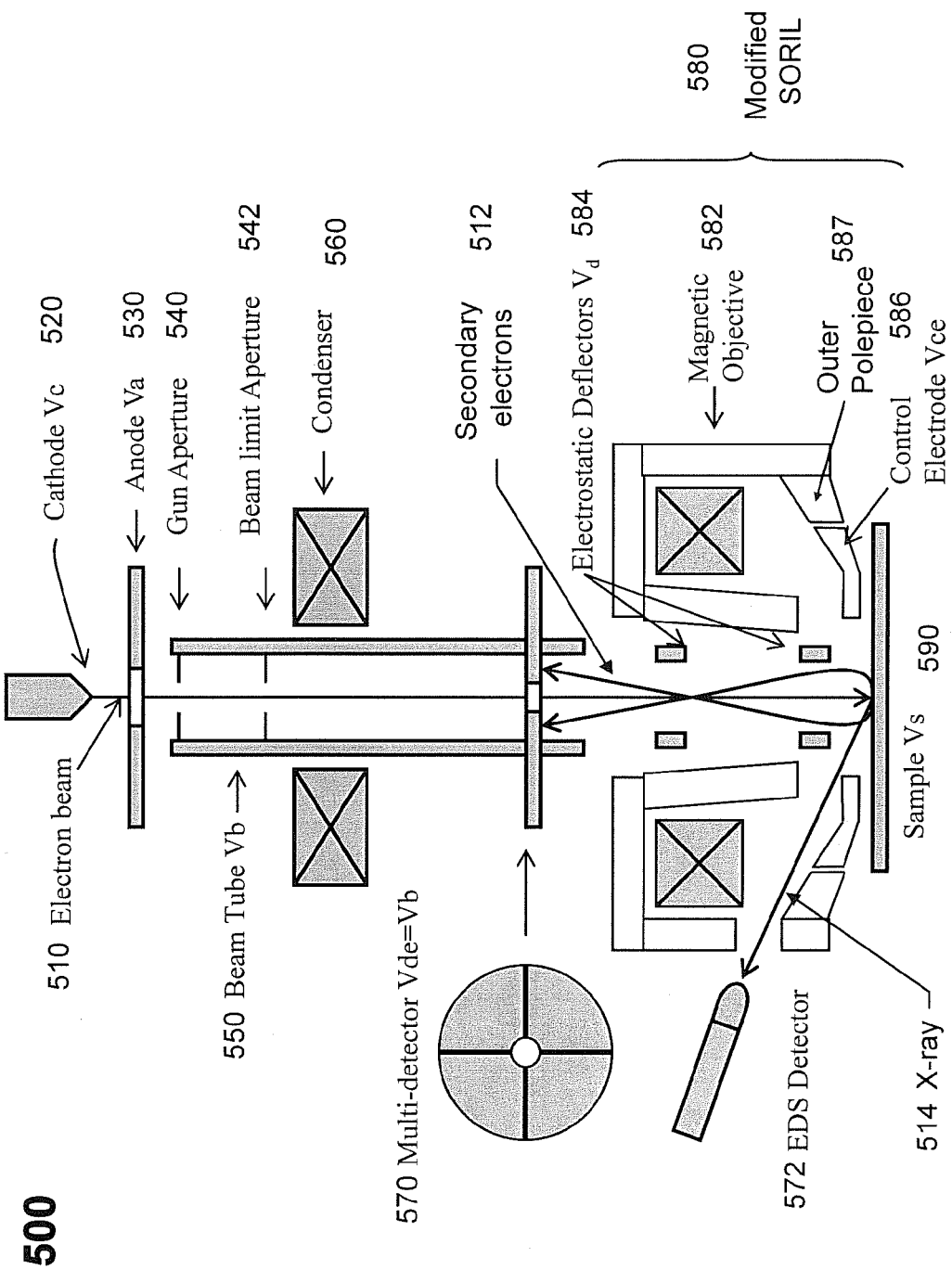
Fig. 5: System Structure of the secondary embodiment of Present Invention

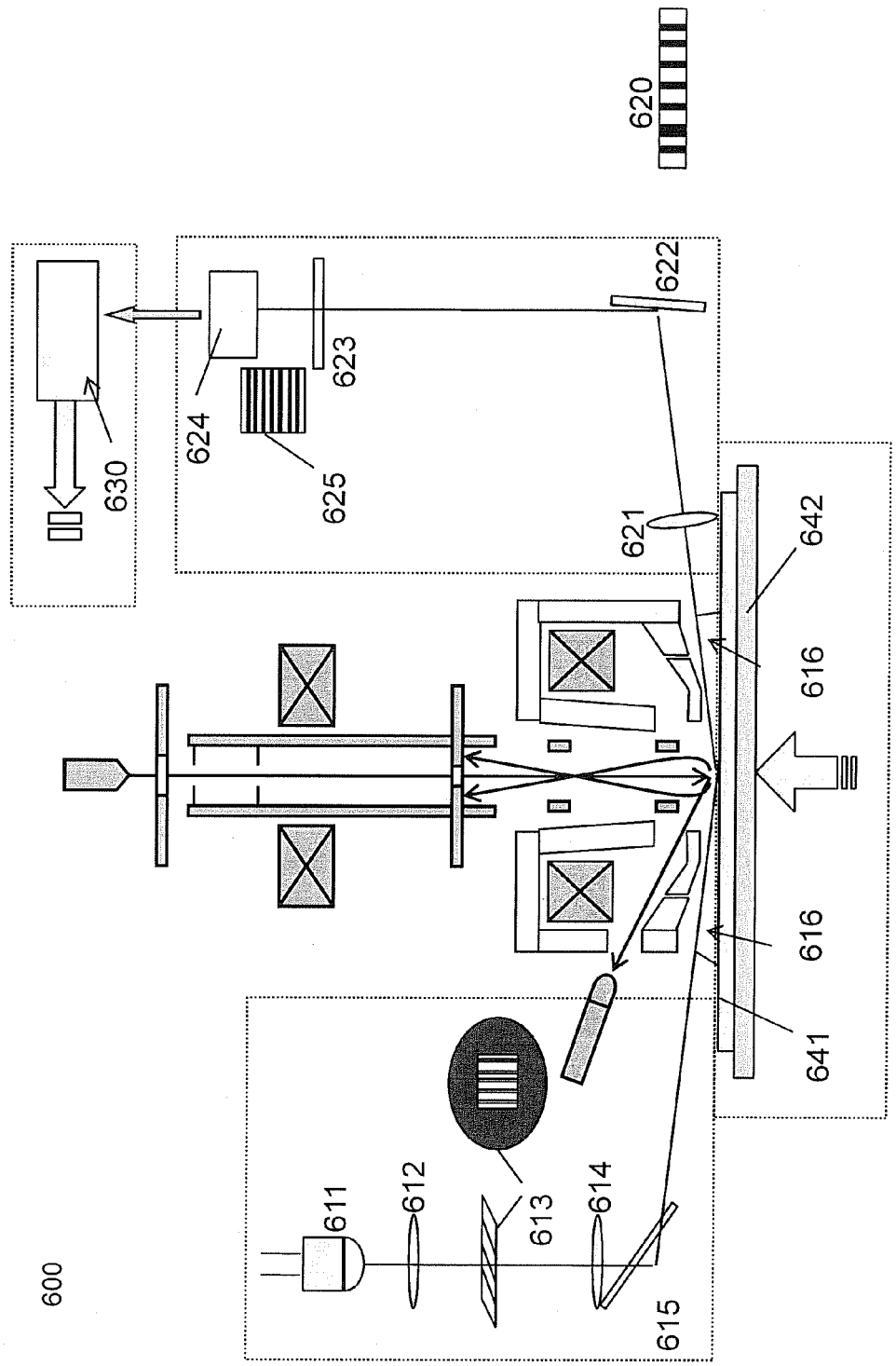
Figure 6. The new designed scanning electron microscope wafer review system.

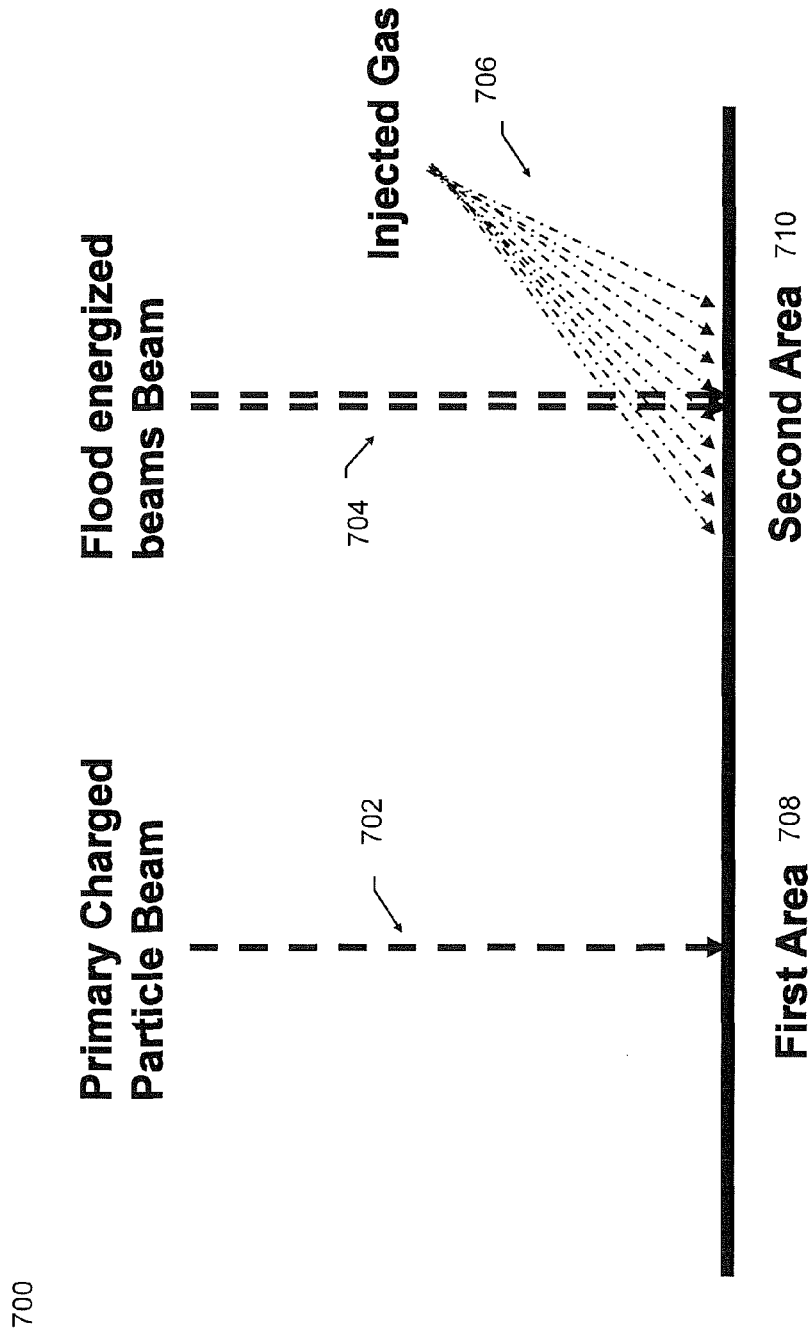
Figure 7. Details of the wafer surface charging control system. The flood energized beam ionize the molecule of injected gas to neutralize the surface charging under flood charge particle beam area. The whole surface of a wafer or the surface of review sampled areas are conditioned before defect review.

E-BEAM DEFECT REVIEW SYSTEM

CROSS-REFERENCES TO RELATED APPLICATIONS

This application relates to U.S. patent application Ser. No. 12/024,033, filed Jan. 31, 2008, entitled "Smart Defect Review for Semiconductor Integrated Circuit"; U.S. patent application Ser. No. 12/257,304, filed Oct. 23, 2008, entitled "A Charged Particle Beam Apparatus", now U.S. Pat. No. 7,960,697, entitled Electron Beam Apparatus,; U.S. patent application Ser. No. 11/759,138, filed in Jun. 6, 2007, entitled "Optical Auto Focusing System and Method for Electron Beam Inspection Tool", now U.S. Pat. No. 7,767,982; and U.S. patent application Ser. No. 12/232,834, filed Sep. 25, 2008, entitled "Method for Regulating Scanning Sample Surface Charge in Continuous and Leap-and-Scan Scanning Mode Imaging Process" now U.S. Pat. No. 7,973,283.

FIELD OF THE INVENTION

The present invention relates to a defect review system, and/or particularly, to an apparatus and method of defect review sampling, review method and classification on a semiconductor wafer or a pattern lithography reticle during integrated circuit fabrication. However, it would be recognized that the invention has a much broader range of applicability.

BACKGROUND OF THE INVENTION

Charged particle beam apparatus typically employs a scanning electron microscopy (SEM), which is a known technique used in semiconductor manufacturing. Defects can occur on the mask or wafer during the semiconductor fabrication process, which impact yield to a great degree. Defect inspection systems and defect review systems are two significant means for semiconductor yield management.

Defect inspection system detects particles, pattern anomalies (or defects), and process-induced anomalies and typically detection results from the inspection systems are fed to defect review systems. The information usually is anomalies location with respect to the pattern of semiconductor devices or "defect map" of the device. Defect review system according the defect map further reviews the defect with higher magnification and superior resolution then analyzes defect root causes with Energy Dispersive Spectrometer (EDS). However, an electron beam (e-beam) defect review station is not only receiving defect maps from electron beam inspection system but in the most cases also receiving defect maps from optical defect inspection system.

Beside the higher resolution image, stereo imaging detection for topography analysis (which tells whether defects are protrusion or depression) is also a required function in a defect review system. In addition, wafer surface charging due to electron impinging sample surface is another issue that affecting imaging quality.

In the software portion of a review system, the automatic defect review process is the core technique of success. After loading the defect map, automatic defect locating (ADL), defect review and defect classification (die to die comparison or die to database comparison) are very complicated and time consuming. What is needed is a system and method to address the above-identified issues. The present invention addresses such a need.

SUMMARY OF THE INVENTION

The present invention relates to a defect review system, and/or particularly, to an apparatus and method of defect review sampling, review method and classification on a semiconductor wafer or a pattern lithography reticle during integrated circuit fabrication. However, it would be recognized that the invention has a much broader range of applicability.

This and other objects are achieved in comparing a reviewed image with a reference image pick-up through a smart sampling filter. In one embodiment, a clustering computer system is disclosed, the system based on high speed network will provide data cache and save operation time and memory. In another embodiment, a smart review sampling filter is disclosed, the smart review sampling filter automatically relocate abnormal pattern or defects and classify the device location extracted from design database and/or from golden die image on the same substrate. An additional function to enhance the processing speed is that care areas according to the customer predetermined defect of interest (DOI) are loaded into the host computer to screen out defects that are not fall in the care areas.

The column of the present defect review system adopts the modified SORIL type objective lens to ameliorate aberration at large field of view and under electric drifting. This column provides solution of improving throughput during sample inspection, review or material identification by utilizing fast scanning ability of SORIL and provides a large voltage difference between sample and detectors. This design makes the secondary electrons impinging on the detector with large kinetic energy which is better for getting higher detection gain. Thereafter provide higher signal to noise ratio to benefit image quality. In addition, the column also provides solution of topography analysis by adopting and modifying multi-channels detector and provides material analysis with equipped EDS.

One embodiment adopts an optical auto focusing system to compromise micro height variation due wafer surface topography. And yet another embodiment adopts surface charge control system to regulate the charge accumulation due to electron irradiation during the review process.

The present invention provide a defect review system with smart review sampling filter to locate the defect more efficiently, a review station column that can provide stereo image with high resolution, an auxiliary optical grating focusing accessory to enhance micro-defocusing according surface topography, equip with EDS for material analysis ability and a surface charge regulation method to meet these needs.

BRIEF DESCRIPTION OF DRAWINGS

The present invention will be readily understood by the following detailed description in conjunction with the accompanying drawings, wherein like reference numerals designate like structural elements, and in which:

FIG. 1 is a schematic diagrammatic representation of a function chart of a prior art review system.

FIG. 2 is a schematic diagrammatic representation of a function chart of a present invention.

FIG. 3 is a schematic diagrammatic representation of a typical pattern wafer.

FIG. 3a is a schematic diagrammatic representation of an enlarged figure of a die.

FIG. 4 is a schematic diagrammatic representation of a schematic diagrammatic representation of care areas within a die according to an embodiment of the present invention.

FIG. 5 is a schematic diagrammatic representation of the modified SORIL column used of the present invention.

FIG. 6 is a schematic diagrammatic representation of the review system with optical focusing sub-system of the present invention.

FIG. 7 is a schematic diagrammatic representation as an example of the surface charging regulating method that equipped to the present invention.

DETAILED DESCRIPTION OF PREFERRED EMBODIMENTS

Reference will now be made in detail to specific embodiments of the invention. Examples of these embodiments are illustrated in accompanying drawings. While the invention will be described in conjunction with these specific embodiments, it will be understood that it is not intended to limit the invention to these embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations are not described in detail in order not to unnecessarily obscure the present invention.

The present invention relates to a defect review system, and/or particularly, to an apparatus and method of defect review sampling, review method and classification on a semiconductor wafer or a pattern lithography reticle during integrated circuit fabrication. However, the method and algorism disclose in the present invention may also apply to defect inspection system.

Defects Sampling, Defects Comparison and Defects Classification System

A typical conventional automatic defect review process as shown in FIG. 1 includes the following steps:

(1) Loading the wafer 102 to SEM and obtaining the inspection result to the host computer 110 (the defect map file is obtained from other inspection tool); (2) Aligning the wafer and defining the die origin; (3) Defect offset correction 108; (4) Beam or light condition setup; (5) Review defect sampling setup; (6) Automatic defect locating (ADL) setup 112; (7) Review imaging condition setup 106; (8) Defect classification 114, which can be auto, semi-auto, and manual classification; (9) Setting up data output role and location 116; and (10) Unloading the wafer.

To review all of the defects picked from an inspection tool is very time consuming and unnecessary most of the time.

The defect review system of present invention adopts "the smart review sampling filter" and "universal defect location unit" disclosed by Jau et al. in U.S. patent application Ser. No. 12/024,033 filed on Jan. 31, 2008 to improve the performance of review defect sampling setup, automatic defect locating method and defect classification.

Regarding the step of review defect sampling setup, the most common practice in semiconductor production line monitoring is randomly sampling 50 or 100 defects from a inspection result to review. More complicated sampling also includes random defect selection by percentage, by defect size and by defect classification (rough bin), by defect cluster, and etc. The common problem for such sampling is that tool user cannot avoid reviewing defects located at "unimportant areas" or locations that are not cared by the line monitoring. Valuable tool time may be wasted by reviewing unimportant non-killer defects.

One key feature is "smart review sampling filter" 212 (FIG. 2). All defects are analyzed by the "universal defect location unit" 214 with the data extracted from design database before execute automatic review job. Defect sampling is executed by the result of smart review sampling filter. Both smart review sampling filter and defect plan are setup during recipe construction. With smart review sampling filter, following can be achieved:

(1) A tool user can avoid using valuable time to review a defect located at an unimportant position, such as a defect located on the scribe line (the space between dies). The user can set up their review sampling to review a defect only on a defined sensitive area, such as a high aspect ratio (HAR) contact area.

(2) Defect distribution on a particular device unit will be displayed, such as defect distribution on SRAM, which can help the user to evaluate their process.

(3) Defect density on selected areas or devices will be given, such as defect density on SRAM.

(4) Defects that may impact next subsequence layers will be indicated and can be sampled for review.

Currently design database 220 will become very large when design feature are 32 nm or less. The design database sometimes will reach more than 200 giga-data. One aspect of current invention is high speed data cache based on clustering computer structure. The design database may be saved in some separated computers which will be linked by high speed network Based on reviewed defect location information, each computer will just cache defect location related design data, instead of needing to load whole design database into memory.

The most common problem for the automatic defect locating (ADL) setup is that the procedure is time consuming. In order to review one defect, the stage generally needs to move two times (visit reference die of the same location and the defect) and take three images (low magnification reference image, low magnification defect image, high magnification defect image).

Another key feature is Universal Defect Locating Unit (UDL) 214. Not only random defects but also systematical defects can be automatically located. The UDL method comprises comparing the defect image with the design layout from the database to locate the exact defect location. With this method, the two common problems existing in the current defect review tool can be overcome:

(1) Based on the proposed method, the stage needs to move fewer times to review a defect. Thus, the throughput will be improved with this method.

(2) The image converted from design database is not impacted from process variation or repeating defects, such as mask defects or an Optical Proximity Compensation (OPC) problem. A system and method in accordance with the present invention provides the capability to review the defect file generated from die to database comparison.

Regarding step of defect classification, the smart review sampling filter 212 provides user with an opportunity to automatically classify defect according to where a defect is located as shown in FIG. 2. For example, there are two types of contact in one die: a regular contact and a high aspect ratio (HAR) contact. The smart review sampling filter 212 in accordance with the present invention can determine whether that defect is a regular contact over etch or an HAR contact under etch. Accordingly, the two types of defect have different meanings for the process.

An additional function is adding to the smart sampling filer 212 in the present invention. In order to further enhance the processing time, care areas are defined according to the customer's defect of interest (DOI). A DOI could be, for example, an open defect, a short defect, a junction leakage defect, or a particle defect with a circuit. This information could be manually select from a preset table or automatically load into the host computer with the defect map. The smart sampling filer and the UDI are then setup the review plan and sampling defects only fall in the care areas to review. Therefore much efficiently reduce the defect locating and image comparing time. FIG. 3 illustrates a typical pattern wafer, FIG. 3a shows an enlarged figure of a die, and FIG. 4 is a schematic diagrammatic representation of care areas 406 within a die.

As soon as defects are inspected in the most sensitive device by the apparatus or caught from automatic defect relocation in the apparatus those defects can be automatically highlighted and a warning signal can be sent to related person from internet. The most sensitive device can also be defined in the smart review sampling filter 212.

Imaging System

The imaging column of the present review station is adopted from Chen et al. U.S. patent application Ser. No. 12/257,304 filed in Oct. 23, 2008 entitled "A Charged Particle Beam Apparatus". It is a modified Swing Objective Retarding Immersion Lens (SORIL). Besides the original advantages such as less off-axis aberrations in scanning imaging, large field of view, the modified SORIL system 500 also increase the following functions.

The modified SORIL system 500 enhance the imaging resolution by (a) equip a field emission cathode 520 with a large tip radius to reduce electron emission current density without reducing angular intensity; (b) applying a large accelerating voltage across ground potential between the cathode 520 and anode 530 to reduce total emission current without reducing angular intensity; (c) positions the beam limit aperture 542 before condenser lens 560 to reduce Coulomb effect; (d) applies a, high positive beam tube 550 bias to reduce objective aberrations and Coulomb effect; (e) modifies the outer polepiece 587 of the SORIL lens 580 to ameliorate aberration at large field of view and under electric drifting.

The modified SORIL system 500 provides a solution of topography analysis by adopting and modifying a multi-channels detector 570. Signals from the different channels can generate a stereo image in combination, finally ensuring a topography analysis of the defects of interest. The system and method can largely reduce on-axis and off-axis aberrations in scanning imaging, and as a result the field of view with high resolution is increased. The modified SORIL system 500 also equipped Energy Dispersive Spectrometer (EDS) detector 572 to collect the X-ray 514 generated from the position that impinged by the electron beam to reveal material characteristics The modified SORIL system 500 is illustrated in FIG. 5.

Focusing Control System

In one embodiment a focusing sub-system 600 is utilized to perform micro-focusing due to the wafer surface topology. The sub-system is adopted from Wang et al. in title of "Optical Auto Focusing System and Method for Electron Beam Inspection Tool", U.S. patent application Ser. No. 11/759,183 filed in Jun. 6, 2007. FIG. 6 illustrates the focusing sub-system with the SORIL system 500. This focusing control system 600 projects image of a grating 613 with optical source 611 onto sampling area 641 and collects the reflecting grating image 625 by charge-coupled device (CCD) camera 624. The collected image is then compared with the previous image, if the position variation is refer to the spot's height variation and adjusting the focus of the spot accordingly. The algorithm may eliminates influence from wafer tilt, rotation and surface topography induced error and provides the surface height determination within 3σ, which implies to 99.74% accuracy. Where σ is the standard deviation.

Surface Charge Control System

A solution provides solution for surface charge control is provided by adopting Wang et al. in title "Method for Regulating Scanning Sample Surface Charge in Continuous and Leap-and-Scan Scanning Mode Imaging Process", U.S. patent application Ser. No. 12/232,834 filed in Sep. 25, 2008 to regulate surface charge accumulation during the review process.

Gaseous molecules 706 are injected under the flood energized beam 704, rather than under the primary charged particle beam 702. The flood beam 704 ionizes the molecule of injected gas 706 to neutralize the surface charging under electron beam irradiation area 710. The whole surface of a wafer or the surface of review sampled areas is conditioned before defect review. In one example, the flood energized beam 704 may be suitable for ionizing the gaseous molecules 706, for example but not limited to, UV, laser, charged particle beam, and etc. Next, the gaseous molecules ionize upon being bombarded by the energized beam so as to regulate a surface charge that would be induced by the scanning of the sample surface. In this example, the gaseous molecules 706 may be, for example but not limited to, inert gas, air, water, and etc. This method is particularly important for not impact on the image resolution and the primary beam column vacuum condition. FIG. 7 illustrates the relative position of the flood beam and primary beam of the present defect review system.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended.

What is claimed is:

1. An apparatus comprises:
    an imaging unit to image a wafer to be reviewed, wherein imaging unit is the modified SORIL column;
    a focusing sub-system to do micro-focusing due to a wafer surface topology, wherein the focusing sub-system verifies the position of a grating image reflecting from the wafer surface to adjust the focus;
    a surface charge control to regulate the charge accumulation due to electron irradiation during the review process, wherein the gaseous molecules are injected under a flood gun beam rather than under a primary beam;
    a storage unit for storing wafer design database; and
    a host computer to manage defect locating, defect sampling, and defect classifying, wherein the host computer and storage unit are linked by high speed network.

2. The apparatus of claim 1, wherein the host computer and storage database is a clustering computer system based on high speed network.

3. A system for automatic defects review on semiconductor integrated circles wafer comprising:
    an imaging unit to image a wafer to be reviewed, wherein imaging unit is the modified SORIL column;
    a focusing sub-system to do micro-focusing due to a wafer surface topology, wherein the focusing sub-system verifies the position of a grating image reflecting from the wafer surface to adjust the focus;
    a surface charge control to regulate the charge accumulation due to electron irradiation during the review process, wherein the gaseous molecules are injected under a flood gun beam rather than under a primary beam;
    a storage unit for storing wafer design database; and a host computer to manage defect locating, defect sampling, and defect classifying, wherein the host computer and storage unit are linked by high speed network.

4. The system of claim 3, wherein the defect locating, and defect sampling, includes a Smart Review Sampling Filter.

5. The system of claim 3, wherein the defect classifying is can be based on the Universal Defect Locating Unit.

* * * * *